United States Patent [19]

Hicks

[11] Patent Number: 5,425,123
[45] Date of Patent: * Jun. 13, 1995

[54] MULTIFIBER ENDOSCOPE WITH MULTIPLE VIEWING MODES TO PRODUCE AN IMAGE FREE OF FIXED PATTERN NOISE

[76] Inventor: John W. Hicks, 312 Howard St., Northboro, Mass. 01532

[*] Notice: The portion of the term of this patent subsequent to Jul. 21, 2009 has been disclaimed.

[21] Appl. No.: 94,509

[22] Filed: Jul. 20, 1993

[51] Int. Cl.⁶ .......................... G02B 6/00; G02B 6/36
[52] U.S. Cl. ................................................... 385/117
[58] Field of Search .............................. 385/115–117

[56] References Cited

U.S. PATENT DOCUMENTS 4,327,738  5/1982  Green et al. .................. 128/660
5,074,642 12/1991  Hicks ............................ 385/116
5,133,035  7/1992  Hicks ............................ 385/117

OTHER PUBLICATIONS

Hosono, Toshio; Yamaguchi, Shoji; Mori, Kensuke; Improvement of Crosstalk Characteristics of Image Fiber, Apr., 1985, Electronics and Communications in Japan, Part 2, vol. 69, No. 3, pp. 10–19.

Primary Examiner—Akm E. Ullah
Attorney, Agent, or Firm—Samuels, Gauthier & Stevens

[57] ABSTRACT

A fiberoptic endoscope scanning system with multiple scanning modes. The first mode is a multifiber scanning along its longitudinal axis and a second scanning mode is a chromatic scan comprising a prism and/or grating at the distal end of the endoscope. The multiple scanning modes result in superior improvement in the image scan. The superior improvement in the clarity of the image scanned.

22 Claims, 2 Drawing Sheets

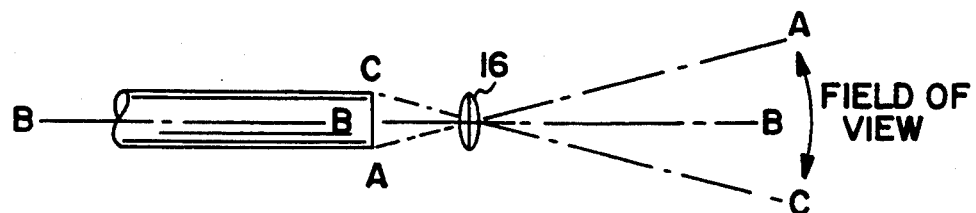
FIG. 1
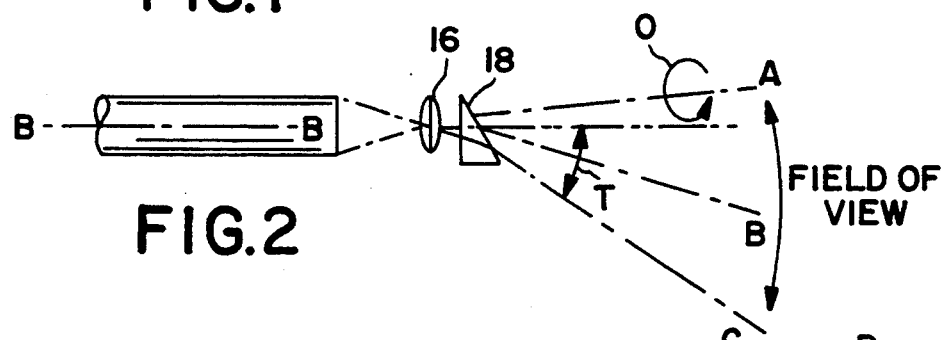
FIG. 2
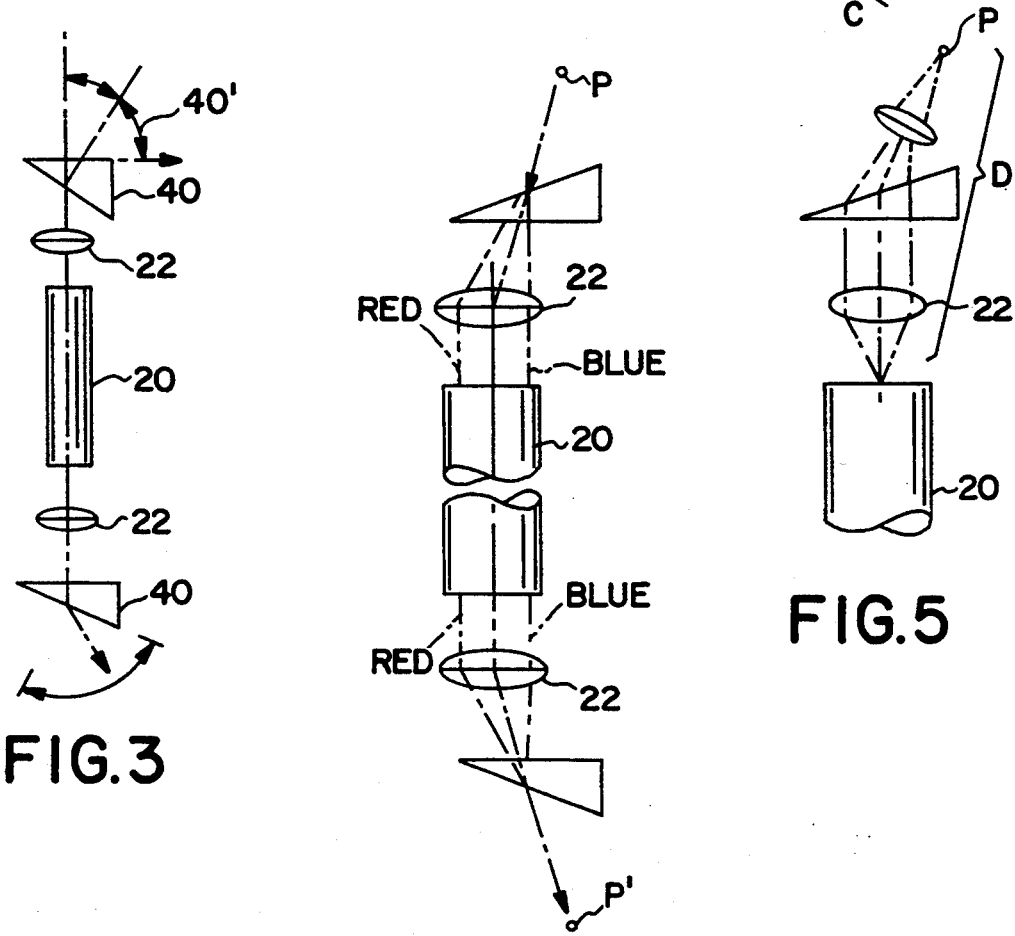
FIG. 3
FIG. 4
FIG. 5

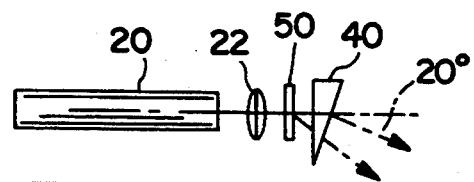
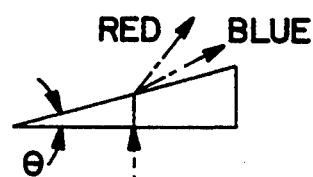
FIG.6  FIG.7
FIG.8
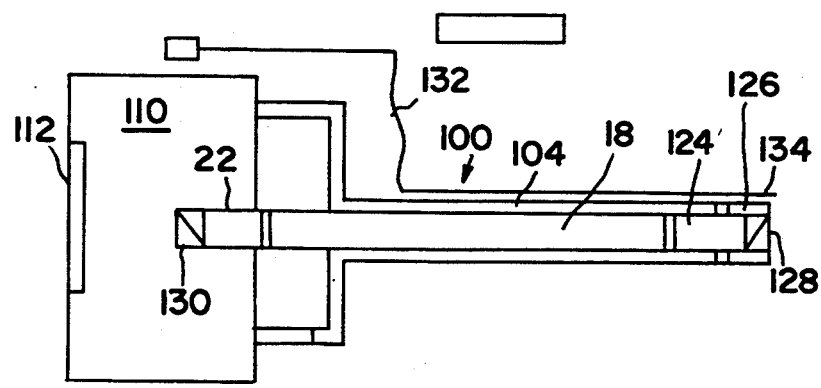
FIG.9

MULTIFIBER ENDOSCOPE WITH MULTIPLE VIEWING MODES TO PRODUCE AN IMAGE FREE OF FIXED PATTERN NOISE

FIELD OF THE INVENTION

The present invention relates to endoscopic devices and in particular to a scanning multifiber endoscope which eliminates the noise pattern inherent in prior art optic or multifiber endoscopes.

BACKGROUND AND BRIEF SUMMARY OF THE INVENTION

The transmission of light through thin fibers of which fiber glass or plastics has resulted in a variety of instruments for the visualization of otherwise inaccessible organs and tissues inside the human body. Such instruments are broadly referred to as endoscopes and have been useful in the diagnosis and treatment of, for example, gastro intestinal and respiratory diseases.

Fiberoptic endoscopes were first introduced about thirty years ago. Although they have gained wide acceptance where flexibility is required, medical personnel still prefer to use rod lenses or other alternatives. The reason being that they are annoyed by the fixed mosaic structure of a fiberoptic image. Also in most applications, the resolution of present fiberoptic endoscopes is generally inferior to other alternatives.

It is known in the art to scan with fiberoptics. If a multifiber is rotated, a concentric noise pattern is superimposed on the image. If the multifiber is not moved, a mosaic-like noise pattern is superimposed on the image.

In my issued U.S. Pat. No. 5,074,642, which patent is hereby incorporated by reference in its entirety into this disclosure, a multifiber endoscope was disclosed with much improved resolution for a given diameter and which partially eliminated the fixed pattern noise typical of fiber endoscopes. However, I have found that even with rotational scanning there is still a residual fixed pattern streakiness comprising concentric circles even though the individual fibers themselves are no longer visible. Also, a small area near the axis of rotation has a very pronounced fixed pattern noise.

My issued U.S. Pat. No. 5,133,035, which patent is hereby incorporated by reference in its entirety into this disclosure, embodied a multiple-scanning multifiber assembly which substantially reduced or eliminated the noise inherent in prior art multifiber endoscopes. The multiple scanning comprised either a rotary and a chromatic scan or two rotary scans.

In the present invention, it has been discovered that a clear image is produced without a rotational scan of the multifiber. That is, both the multifiber and the prism and/or grating remain fixed.

BRIEF DESCRIPTION OF THE DRAWINGS

FIG. 1 is an illustration of a multifiber and lens;

FIG. 2 is an illustration of a multifiber and lens and prism with a tipped field of view;

FIG. 3 is a schematic illustrating an image produced on the tip of the fiberscope FIG. 4 is a schematic of an optical arrangement where the fiberscope is focused at a finite object;

FIG. 5 is a schematic of a diffraction grating prism combination;

FIG. 6 is an illustration of the angular tilt of a prism;

FIG. 7 is an illustration of the angular tilt of the grating;

FIG. 8 is a schematic of alternative optics at the proximal end; and

FIG. 9 is illustrative of an endoscope system embodying the device of the invention.

DESCRIPTION OF THE PREFERRED EMBODIMENT(S)

In the following disclosure, various combinations of multifibers, lenses and/or prisms and/or gratings will be described. Further, the techniques for the illumination of the object to be viewed and the various schemes for processing the signals received from the viewed object and to display the object are well within the skill of the art.

The multifiber described herein for the preferred embodiment has the optical characteristics of multifiber in my parent application, namely the fibers having distinct indices of refraction. Although this form of multifiber is preferred, multifibers wherein each of the fibers have the same indices of refraction can be used or combinations of fibers having different refractive indices can be used in different arrays. Where necessary, for a full understanding of the invention, the specific optical properties of lenses, gratings and/or prisms are described.

It is known that the field of view can be increased by tipping, such as with a mirror. However to tip 45° and still be able to view in the forward direction is not easy to do with any simple array of mirrors that do not take up a lot of space.

An ordinary diffraction grating, generally will look both ways unless it is blazed to look preferentially in one or the other direction. If the diffraction grating is made holographically, then blazing is easily accomplished. In any case, unwanted negative orders can be further suppressed by illuminating only in the desired direction. Both the prism and the grating have strong chromatic effects. In the case of the prism, the blue light is tipped more than the red light and in the case of the grating, the red light is tipped more than the blue light. These chromatic effects are corrected for at the proximal end.

With the structure to effect the tipping action, a chromatic scan is also accomplished. Chromatic scan, as used in the disclosure, defines the optical spread of the wavelengths. Because the image of one point is spread out in a rainbow and then travels through many fiber cores, the effect is much the same as if the fiber had been scanned in the tipped direction. When the final image is viewed, the fiber core structure almost disappears and the resolution is increased almost as if the bundle had been rapidly scanned. There is still dimension just as there is with a one dimensional scan. However, if the linear streaking Parallel to the scanned as there is with a one dimensional fiber is scanned about its axis this streakiness also disappears.

Referring to FIG. 1, a multifiber 10 is shown in combination with a lens 16. The central ray is shown as B and the field of view is defined by A-C.

In the preferred embodiment, either a prism and/or diffraction grating (prism/grating) is used in connection with the multifiber to tip the central ray(s) and thereby expand the field of view. Normally, the central ray in a multifiber endoscope is coincident with the fiber axis. In the present invention, the central ray tipped away from the fiber axis and the ray is also dispersed.

Referring to FIG. 2, a prism 18 tips the field view. The tip angle is shown as T and the field of view defined, as in FIG. 1, A–C. As can be seen with reference to FIG. 2, a much larger field of view is swept.

Where A is tipped to be coincident with the axis of rotation B—B of the multifiber, the field of view is doubled.

If A is tipped more than this, below B–B with reference to FIG. 2, there will be a black hole in the image. If A is tipped less than this, the image will be brighter in the area that is overlapped. This overlapped area is shown by the arrow 0 in FIG. 2. This can be partially compensated for by providing less illumination in the overlapped area of the object or by image processing (when the display is video, not directly viewed).

Referring to FIG. 3, in one embodiment of the invention, a multifiber 20 has at the proximal and distal ends, lenses: 22, 0.5 mm diameter and a refractive index of 2.0. High dispersion prisms 40 having a refractive index of 1.8 which tips the field of view 30.5° are used. The multifiber is as described in my '642 patent. However, it is to be understood that any multifiber where the fiber cores have the same or different refractive indices may be used. A suitable multifiber having fiber cores of the same refractive index would be a commercially available multifiber, such as a Sumitomo multifiber.

Referring to FIG. 4, the image produced on the face of the multifiber 18 by a point object, P, at infinity is shown. The point, p1, is spread into a linear rainbow. At the proximal end, the rainbow is recombined to form the point, P. The same spreading and recombining is true of a grating. Obviously the optics at the proximal and distal ends need to be identical or at least conjugal.

The prisms or gratings produce aberrations if the lens does not focus the face of the bundle to infinity. These aberrations are severe astigmatisms and something comparable to spherical aberrations. If the instrument must be focused to a finite object at a distance, D, of say 1 cm, referring to FIG. 5, another lens 40 is added. The lens 40 has a focal length of 1 cm to accommodate the object. Again the same optics is provided at the proximal end in that the optics must be identical up through the prism or grating but not necessarily beyond that.

When the multifiber looks straight forward or is only slightly tilted and a chromatic scan is used, a combination of a prism and a grating can be used. The prism has much less dispersion (much less spread in angle between red and blue) for the same tip angle than has the grating. Little or no tipping with increased dispersion, for chromatic scanning, is achieved. The prism is preferably a high index glass. Such glasses are characteristically absorbing in the visible spectrum but the prism thickness is exceedingly small because of the small diameter of the fiberscope. So, absorption isn't a problem. Indices of refraction of 1.8 are commercially available.

Endoscopes of the invention are preferably designed so that they can be easily inserted into and removed from a sleeve such as a hypodermic needle. In this way a needle is inserted into a cavity in a body. A first endoscope is inserted with a nearly hemispheric field of view. When something of particular interest is sighted, the first endoscope can be removed and replaced by another endoscope with a narrower field of view, desired degree of tip and more pixels per unit object area (orientated or tilted in the direction desired). The fiberoptics is relatively inexpensive so these endoscopes can be made as disposable endoscopes.

When using combinations of prisms and gratings, there are certain design considerations. To a first approximation, a holographic grating which tips the principle ray of green light by 45° at the distal end of the endoscope and a holographic grating which tips the principle green ray 22½° at the proximal end together with a distal lens and a proximal lens with a focal length ratio of ½ will be a conjugate pair and accomplish the desired result. But to a closer approximation since $\theta$, sin $\theta$ and tan $\theta$ are not linear functions of each other, this is not exactly true. There are several options. The simplest is to select a second grating which collapses the rainbow fairly accurately and to forget the criteria of keeping any axes of rotation aligned. This will smear and distort the straight ahead part of the image. However, this may be acceptable in some cases. In the body, the dominant color is red. So a good compromise is to collapse the red end of the spectrum accurately at the expense of the blue end. The compromise can be tuned to the actual use.

A particularly preferred embodiment is to use a prism and holographic grating in combination at the proximal end, the grating used mainly to collapse the chromatic scan and the prism used to correct any residual tilt error.

The index of refraction of common glasses changes by 0.01 to 0.04 from the red end to the blue end of the visible spectrum. The higher dispersion glasses (0.03 for example) are called 'flints' and the lower dispersion glasses are The angular tilt produced by a prism is called 'crowns' approximately $d=(n-1)\theta$ where $\theta$ is the prism angle and n is the index of refraction, see FIG. 8. The spread in this in the index times $\theta$ $$\theta d = \Delta n \theta$$

The ratio of $\dfrac{\Delta d}{d} = \dfrac{\Delta d}{n-1}$

This range is from about $\dfrac{1}{50}$ to $\dfrac{4}{50}$

The tilt angle for a grating is shown in FIG. 9 where $$d \sin\theta = \lambda$$

so that for small $\theta$
The change in $\theta$ from red to blue is $$\Delta\theta = \dfrac{\Delta\lambda}{}$$

and $$\dfrac{\Delta\theta}{\Delta} = \dfrac{\Delta\lambda}{\lambda} = \text{which is about 0.5.}$$

With these factors in mind, the tipping and chromatic scan can be tailored for specific viewing situations. The prism can be treated as almost non-dispersive in the first iteration of a design process. For a more precise approximation, the dispersion of the prism can be factored back in. Although it is of the opposite sign to that of the grating and is not the exact shape, it is possible to get an exact combination of tipping and dispersion at two points of the spectrum and have only a small uncorrected deviation in the spectral region between the two points.

At the proximal end, because $\Delta$ is demagnified (by a factor of two for example) relative to the distal end, a combination of prism and grating (and lens focal length) can be found which gives the right tilt and collapses the chromatic scan at two spectral points but with some residual chromatic spread between these spectral points. Those skilled in chromatic aberration and lens design will understand how to make further corrections, for example by using a prism made of two glasses.

In another embodiment, FIG. 9, the problem of scanning out nearly a hemisphere and presenting an image which can be viewed at the proximal end is handled by using a lens 60 at the proximal end with twice the focal length of the lens 62 at the distal end. The longer focal length reduces the field angle and therefore reduces the tilt necessary to keep an axis of rotation at the far end and the axis of rotation at the near end aligned. The 90° total spread at the proximal end is fairly easy to catch with a field lens by conventional lens designs. As disclosed herein, this design collapses the rainbow generated by a ray at angle $\theta$ at the far end into a ray at the near end so an object point becomes a final image point not a rainbow. The problem of field angle correction is less severe if the final image goes to a video camera.

The prior art relating to illumination of fiber bundles, particularly in endoscopes, and the viewing and display of viewed objects is well known in the art and need not be described in detail.

Referring to FIG. 9, a system embodying the invention is shown and comprises a housing 110 with a CCD array 112. The multifiber 20 is secured in a sleeve 104 which is secured to the housing 110. In this embodiment, the selfoc lens 22, 0.5 mm diameter, refractive index 2.0, at the proximal end is adhered to the fiber bundle 18. This lens has about twice the focal length of a distal selfoc lens 124. This distal lens 124 is adhered to the fiber bundle 18. Secured to the extending portion of the lens 124 is a sleeve 126 in which is secured the prism 40, which tips the field of view 30.5° At the proximal end of the fiber bundle 18 and secured to the lens 122 is a prism 130, which tips the field of view about half the angle of the prism 128. A single fiber laser 132 is secured to the outer surface of the sleeve 104. Its end 134 is shaped to illuminate the entire area to be viewed.

In the present invention, any of the prior described embodiments can be used without rotation of the multifiber and without rotation of the associated prism and/or grating. For example, the configurations of FIGS. 3, 4, 5, 6, 8 and 9 can be successfully employed to produce a clear image without any rotation of any of the components including the multifiber, the prism/grating and/or associated optics. Where the multifiber is not rotated, it is considered as viewing the image rather than scanning the image.

The foregoing description has been has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A fiberoptic endoscope scanning system which comprises:
   at least one multifiber for transmitting light from an object within a field of view from the distal end to the proximal end and to scan in a first mode a continuous region of the object;
   distal optics to form an image of the object on the distal end of the multifiber;
   means to effect simultaneously a second distinct chromatic scan to sweep out a region of the object; and
   optics at the proximal end for displaying the image substantially free of noise, the multifiber, the proximal and distal optics and the means to effect the chromatic scan all in optical communication with one another.

2. The system of claim 1 wherein the chromatic scan is non-rotatable.

3. The system of claim 1 wherein the chromatic scan is rotatable.

4. The system of claim 3 wherein the multifiber is rotatable about its longitudinal axis.

5. The system of claim 3 which comprises:
   means to effect the first and second scans at the same angular velocity.

6. The system of claim 1 wherein the means to effect the chromatic scan comprises a prism.

7. The system of claim 1 wherein the means to effect the chromatic scan comprises a grating.

8. The system of claim 1 wherein the means to effect the chromatic scan comprises a grating in combination with a prism.

9. The system of claim 1 wherein the means to effect the chromatic scan includes means to tip the field of view.

10. The system of claim 1 wherein the means to effect the chromatic scan includes means to disperse the principle ray.

11. The system of claim 1 which includes:
    means to mask at least a portion of the multifiber along its Y axis.

12. The system of claim 1 which comprises:
    means for sequentially displaying the light received at the proximal end so that the region of the image scanned at the distal end is reconstructed at the proximal end.

13. The system of claim 1 which comprises:
    means for effecting the scans at the proximal end in synchronism with the scans at the distal end and in a substantially identical pattern.

14. The system of claim 1 which includes proximal optics which are conjugate to the distal optics.

15. The system of claim 1 wherein the multifiber carries the light to illuminate the object whose image is formed in the image plane.

16. The system of claim 1 wherein the multifiber comprises a plurality of adjacent cores having different indices of refraction.

17. A method of scanning an object with a fiberoptic scanning system which includes:
    transmitting light from an object within a field of view from the distal end of a multifiber to the proximal end;
    forming an image of the object on the distal end of the multifiber;
    scanning the object to sweep out sequentially a continuous region of the image in a first scanning mode;
    scanning simultaneously in a second distinct chromatic scanning mode to sweep out the region of the object;
    scanning in the second mode about a second axis displaced from the first axis; and
    displaying the image at the proximal end of the multifiber substantially free of noise.

18. The method of claim 5 wherein the chromatic scan is rotatable.
19. The method of claim 18 which includes:
scanning in the first and second modes at the same angular velocity.
20. The method of claim 17 which includes:
scanning chromatically to tip the field of view.
21. The method of claim 17 which includes:
dispersing the principle ray.
22. The method of claim 17 which includes:
displaying the light received at the proximal end so that the region of the image scanned at the distal end is reconstructed at the proximal end.

* * * * *